(12) United States Patent
Johnson et al.

(10) Patent No.: US 10,085,900 B2
(45) Date of Patent: Oct. 2, 2018

(54) TRAUMA KIT

(71) Applicant: Tactical Medical Solutions, Inc., Anderson, SC (US)

(72) Inventors: Ross Johnson, Anderson, SC (US); Richard Alan Hester, Greenville, SC (US)

(73) Assignee: Tactical Medical Solutions, Inc., Anderson, SC (US)

( * ) Notice: Subject to any disclaimer, the term of this patent is extended or adjusted under 35 U.S.C. 154(b) by 347 days.

(21) Appl. No.: 14/804,769

(22) Filed: Jul. 21, 2015

(65) Prior Publication Data
US 2016/0184148 A1 Jun. 30, 2016

Related U.S. Application Data

(60) Provisional application No. 62/027,975, filed on Jul. 23, 2014.

(51) Int. Cl.
| | |
|---|---|
| *A61F 17/00* | (2006.01) |
| *A61B 50/30* | (2016.01) |
| *A61B 90/92* | (2016.01) |

(52) U.S. Cl.
CPC .............. *A61F 17/00* (2013.01); *A61B 50/30* (2016.02); *A61B 90/92* (2016.02); *A61B 2050/3008* (2016.02); *A61B 2050/318* (2016.02)

(58) Field of Classification Search
CPC ... A61F 17/00; A61B 50/30; A61B 2050/318; A61B 2050/3008; A61B 90/92; A61B 90/90; A61B 50/31

(Continued)

(56) References Cited

U.S. PATENT DOCUMENTS

| | | | | |
|---|---|---|---|---|
| 752,463 | A * | 2/1904 | Morris | B65D 9/34 |
| | | | | 206/803 |
| 1,487,014 | A * | 3/1924 | Davis | A61F 17/00 |
| | | | | 206/459.5 |

(Continued)

FOREIGN PATENT DOCUMENTS

| | | |
|---|---|---|
| CN | 2247518 Y | 2/1997 |
| DE | 4301282 A1 | 1/1993 |

(Continued)

OTHER PUBLICATIONS

English Abstract of CN2247518.

(Continued)

*Primary Examiner* — Steven A. Reynolds
(74) *Attorney, Agent, or Firm* — Cahn & Samuels, LLP

(57) ABSTRACT

An embodiment of the invention provides a trauma kit including a plurality of medical packets, wherein one or more of the medical packets includes treatment instructions, a first tool for treating a medical situation, the first tool being labeled in a first color, and a second tool for treating the medical situation, the second tool being labeled in a second color. The treatment instructions include a first treatment instruction labeled with a first character designated in the first color, and a second treatment instruction labeled with a second character designated in the second color. A treatment sequence chart includes a flow diagram of treatment steps, wherein each of the treatment steps are color-coded to one of the medical packets.

24 Claims, 19 Drawing Sheets

(58) Field of Classification Search
USPC .................................. 206/570, 438, 370, 363
See application file for complete search history.

(56) References Cited

U.S. PATENT DOCUMENTS

| | | | |
|---|---|---|---|
| 1,683,487 A | 9/1928 | Remley | |
| 1,720,170 A | 7/1929 | Davies | |
| 2,448,171 A | 8/1948 | Edmund | |
| 3,058,584 A * | 10/1962 | Marshall | A61B 10/0096 206/229 |
| 3,861,521 A | 1/1975 | Burtz | |
| 3,958,690 A | 5/1976 | Gee, Sr. | |
| 4,386,642 A | 6/1983 | Durbin | |
| 4,513,866 A | 4/1985 | Thomas | |
| 4,545,484 A | 10/1985 | Rohner | |
| 4,788,984 A * | 12/1988 | Marsik | A61B 10/0012 436/65 |
| 4,865,549 A | 9/1989 | Sonsteby | |
| 4,889,238 A * | 12/1989 | Batchelor | B65D 43/169 206/232 |
| 4,986,414 A | 1/1991 | Ashley et al. | |
| 5,102,234 A | 4/1992 | Levy | |
| 5,169,001 A | 12/1992 | Scheibel | |
| 5,207,303 A | 5/1993 | Oswalt et al. | |
| 5,289,919 A * | 3/1994 | Fischer | A61C 19/02 206/366 |
| 5,833,330 A | 11/1998 | Kos | |
| 5,848,700 A * | 12/1998 | Horn | A61F 17/00 206/459.5 |
| 5,850,630 A * | 12/1998 | Wilson | G06F 19/3481 700/90 |
| 6,116,426 A * | 9/2000 | Slonim | A61F 17/00 206/499 |
| 6,382,205 B1 * | 5/2002 | Weinstein | A61M 3/0262 128/200.14 |
| 6,460,702 B2 | 10/2002 | Hammond | |
| 6,640,976 B1 * | 11/2003 | Franks-Farah | A61B 50/31 206/232 |
| 6,957,738 B2 * | 10/2005 | Hammond | A61F 17/00 206/425 |
| 7,624,869 B2 * | 12/2009 | Primer | B65D 5/4233 206/232 |
| 7,967,139 B2 * | 6/2011 | Brinker | A61B 50/30 206/438 |
| 8,047,375 B1 * | 11/2011 | Hartsfield | A45C 13/02 206/581 |
| 8,647,123 B1 * | 2/2014 | Carter | G06F 19/3406 206/570 |
| 2004/0129581 A1 * | 7/2004 | Tompkins | A61K 49/0404 206/223 |
| 2006/0108241 A1 * | 5/2006 | Smith | A62B 99/00 206/223 |
| 2008/0283426 A1 * | 11/2008 | Primer | A61F 13/8405 206/232 |
| 2010/0274205 A1 * | 10/2010 | Morelli | A61M 1/0088 604/290 |
| 2011/0024323 A1 * | 2/2011 | Martorano | A61F 17/00 206/570 |
| 2011/0036746 A1 * | 2/2011 | Bear | B65D 33/004 206/572 |
| 2012/0185276 A1 * | 7/2012 | Shah | A61M 15/009 705/3 |
| 2013/0292294 A1 * | 11/2013 | Wilson | A61F 17/00 206/571 |
| 2015/0027922 A1 * | 1/2015 | Fresco | A61F 17/00 206/570 |

FOREIGN PATENT DOCUMENTS

| | | |
|---|---|---|
| EP | 0730853 A2 | 9/1996 |
| FR | 2634633 A1 | 2/1990 |
| GB | 792087 A | 3/1958 |
| JP | H0568696 A | 3/1993 |

OTHER PUBLICATIONS

English Abstract of DE4301282.
English Abstract of EP0730853.
English Abstract of FR2634633.
English Abstract of JPH0568696.

* cited by examiner

TRAUMA KIT

This application claims the benefit of U.S. provisional Application Ser. No. 62/027,975, filed Jul. 23, 2014, which is hereby incorporated by reference.

BACKGROUND

The present invention is in the field of trauma kits and, more particularly, to medical kits for treating trauma victims in emergency medical situations.

One prior art first aid kit includes a carrying case for storing first aid packs, wherein each of the first aid packs are specifically designed with products appropriate for a particular first aid situation. For instance, the different first aid situations can include breathing, bleeding, shock, head and spine, bone, eye, burn, and bites and stings. An instructional card is provided for each of the different types of packs, wherein the instructional card for each pack is color coordinated in a color unique to and different from the colors for the remaining packs. The instructional card gives quick reference instructions for administration of first aid in these situations.

In addition, a guidebook is provided that also includes instructions regarding the products contained in each pack. The guidebook is color coordinated with the packs such that the instructions in the guidebook are found on pages which have borders matching the color of the pack. The prior art first aid kit further includes an overview card that is likewise color coordinated to assist the user in finding the appropriate pack for the type of first aid situation encountered.

However, once the correct pack is identified, the prior art first aid kit does not assist the user in quickly locating the appropriate products or tools within the pack that are necessary to treat the trauma victim. Medical packs can include a multitude of products for treating the various ailments that a patient may suffer. Such products can include, for example, gauze, wraps, tape, syringes, tubes, as well as different kinds of medicine, bandages, wraps, coverings, and other medical implements. Because first aid kits are not typically designed for one-time use, medical packs often have many duplicates of the same kind of tool.

Once a user opens a pack, he or she is confronted with the task of finding the correct medical implement to be used in the treatment of the patient. Under the stressful and time sensitive conditions that are commonly associated with the treatment of trauma victims, the task of quickly locating the correct tool amongst a myriad of prepackaged, plastic wrapped medical equipment can be an arduous one. Often times, the ability to quickly and easily locate the proper tools in an emergency situation is critical and can be the difference between life and death.

For example, in a situation where a trauma patient is not breathing, the ability to quickly locate the proper tools for restoring the patient's airways can greatly increase the patient's chance of survival. In some circumstances, where a critically injured patient is not breathing, bleeding, and/or heart has stopped beating, fifteen seconds can be the difference between life or death, saving a limb, or avoiding serious brain damage. The time that is wasted searching for equipment inside of a first aid pack can also result in lost time that may otherwise be used for treating other patients. Such circumstances may arise where there is a large number of trauma victims and a limited number of caregivers.

Furthermore, medical packs often include numerous products where the order of application/use is crucial for treating an injury. When a caregiver is not given the proper assistance in locating the appropriate tool, the caregiver can easily apply the tools in the incorrect sequence to the detriment of the trauma victim. For example, it may be crucial that a tourniquet is applied to a patient suffering from massive bleeding prior to the application or use of other medical implements. Without the proper guidance, valuable time, and a large amount of blood, may be lost if the tools in the packet are not used in the proper order. In another example, without the proper guidance, a user treating a patient suffering from serious burns may spend several minutes wrapping a patient's leg with a long bandage and tape, only to later find that it is essential to apply medication, antiseptic, and/or gauze to the wound prior to wrapping with the bandage. Thus, the improper use of the first aid pack can result in the loss of precious time (in minutes) and the waste of non-reusable medical equipment (e.g., bandages).

The instructional card, guidebook, overview card, and packs of the prior art first aid kit fail to provide the user with the proper guidance or assistance needed to quickly locate the appropriate product for treating the injury. Valuable time may be wasted if a caregiver does not know where to locate a specific medical implement in a first aid pack, which can result in the tragic loss of life, limb, blood, and/or skin.

SUMMARY OF THE INVENTION

An embodiment of the invention provides a kit for treating a trauma victim in an emergency medical situation. The kit includes a plurality of medical packets, wherein one or more of the medical packets includes treatment instructions, a first tool for treating a particular medical situation, the first tool being labeled in a first color, and a second tool for treating the particular medical situation, the second tool being labeled in a second color different from the first color.

The treatment instructions include a first treatment instruction labeled with a first character designated in the first color, such that the first treatment instruction is color-coded to the first tool for rapid identification by a user. The treatment instructions further include a second treatment instruction labeled with a second character designated in the second color, such that the second treatment instruction is color-coded to the second tool for rapid identification by the user. In addition, the kit includes a treatment sequence chart including a flow diagram of treatment steps, wherein each of the treatment steps are color-coded to one of the medical packets.

BRIEF DESCRIPTION OF THE SEVERAL VIEWS OF THE DRAWINGS

The present invention is described with reference to the accompanying drawings. In the drawings, like reference numbers indicate identical or functionally similar elements.

DETAILED DESCRIPTION

Exemplary, non-limiting, embodiments of the present invention are discussed in detail below. While specific configurations are discussed to provide a clear understanding, it should be understood that the disclosed configurations are provided for illustration purposes only. A person of ordinary skill in the art will recognize that other configurations may be used without departing from the spirit and scope of the invention.

An embodiment of the invention provides a trauma kit including a plurality of medical packets, wherein each medical packet is specifically designed to treat a particular medical situation (e.g., bleeding, burns, broken bones, etc.). Each medical packet includes treatment instructions and tools (also referred to herein as "medical implements" or "products") for treating the particular medical situation. In order to assist a user in quickly identifying the appropriate tools within the medical kit, the treatment instructions include treatment steps that are labeled with a number and a color. The tool that is to be used in the treatment step is color and number coded with the treatment step to allow for rapid identification of the tool by the user.

For example, a massive bleeding medical pack includes a first treatment step (labeled "1" in orange) that provides instructions for applying a tourniquet, and a second treatment step (labeled "2" in green) that provides instructions for applying a bandage. To quickly locate the appropriate tool, the massive bleeding medical pack includes at least one tourniquet that is labeled "1" in orange and at least one bandage package that is labeled "2" in green.

Therefore, the numerical and color coded labeling of the treatment steps and associated tools in the medical packet provide the user with the necessary guidance that may be essential for quickly locating the appropriate tools within the pack to treat the trauma victim. In an emergency situation where time is of the essence, the ability to quickly and easily locate the proper tools is critical and can be the difference between life and death, or loss of limb, blood, and/or skin.

Figure 1:
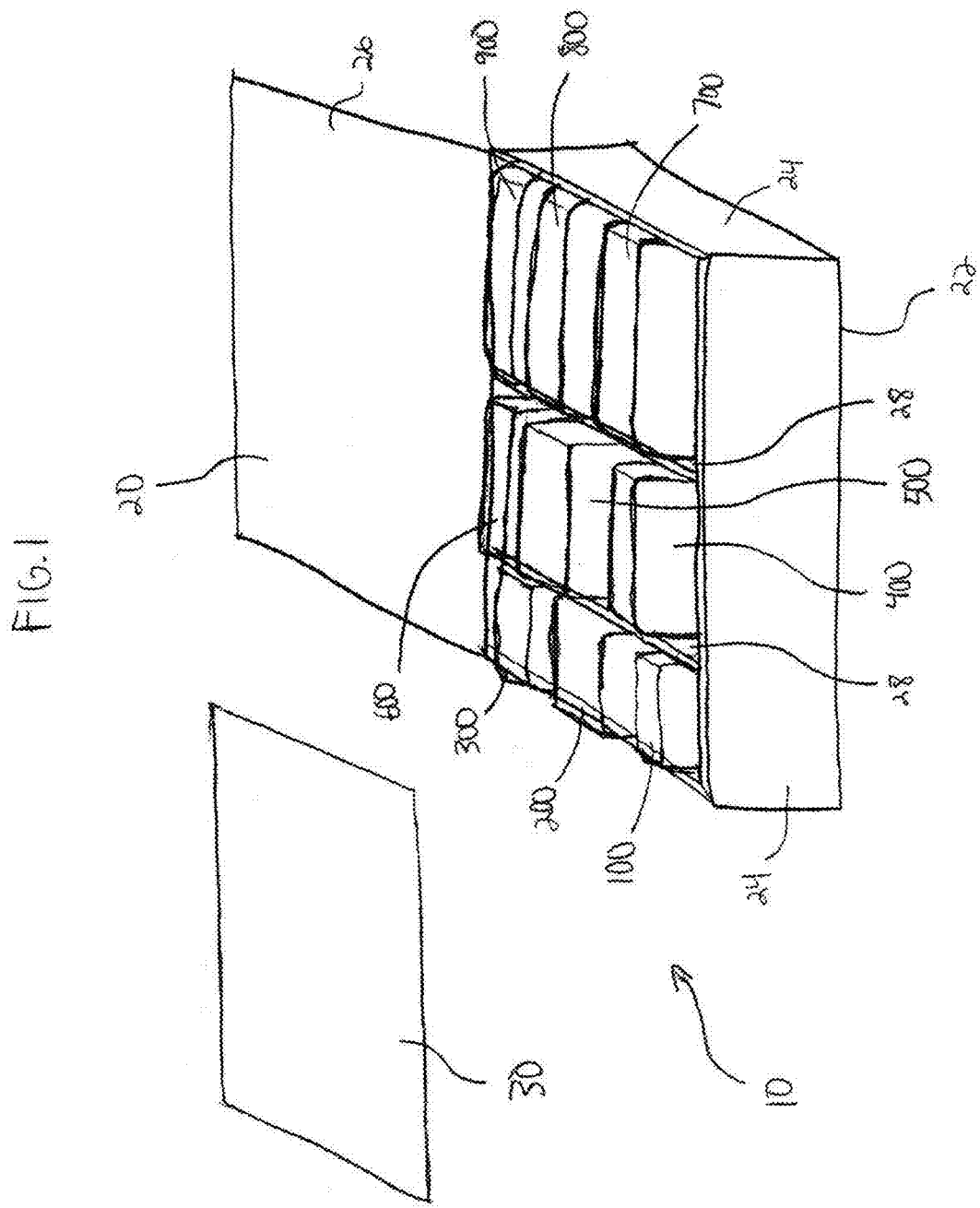
FIG. 1 illustrates a trauma kit according to an embodiment of the invention.

FIG. 1 illustrates a trauma kit 10 having a case 20 for storing medical packets therein. In at least one embodiment of the invention, the trauma kit 10 includes a treatment sequence chart 30, a caregiver protection packet 100, a massive bleeding packet 200, a breathing packet 300, a chest/torso injury packet 400, a wound care packet 500, a burns packet 600, a broken bones packet 700, an eye injury packet 800, and a casualty care packet 900. It is recognized that in alternative embodiments, the trauma kit 10 can include more medical packets, less medical packets, or combined medical packets.

In at least one embodiment of the invention, the case 20 includes a bottom portion 22, sidewalls 24, a lid 26 to allow easy access to the contents of the case 20, and one or more dividers 28 that form compartments for storing the medical packets 100-900 therein. The case 20 can be formed from flexible material (e.g., nylon), semi-flexible material (e.g., plastic), rigid material, or a combination thereof.

In at least one embodiment, the dividers 28 are detachable in order to adjust the sizes of the storage compartments. More specifically, a strip of hook and loop fasteners can be disposed on the inner surfaces of at least two opposing sidewalls 24. Each divider 28 can have hook fasteners disposed on their respective ends that can be removably attached to the loop fasteners on the sidewalls 24. Thus, a user can adjust the sizes of the storage compartments by repositioning the divider(s) 28 along the strips of loop fasteners. This may advantageous as the sizes of the medical packets change with use of the trauma kit 10.

Figure 2:
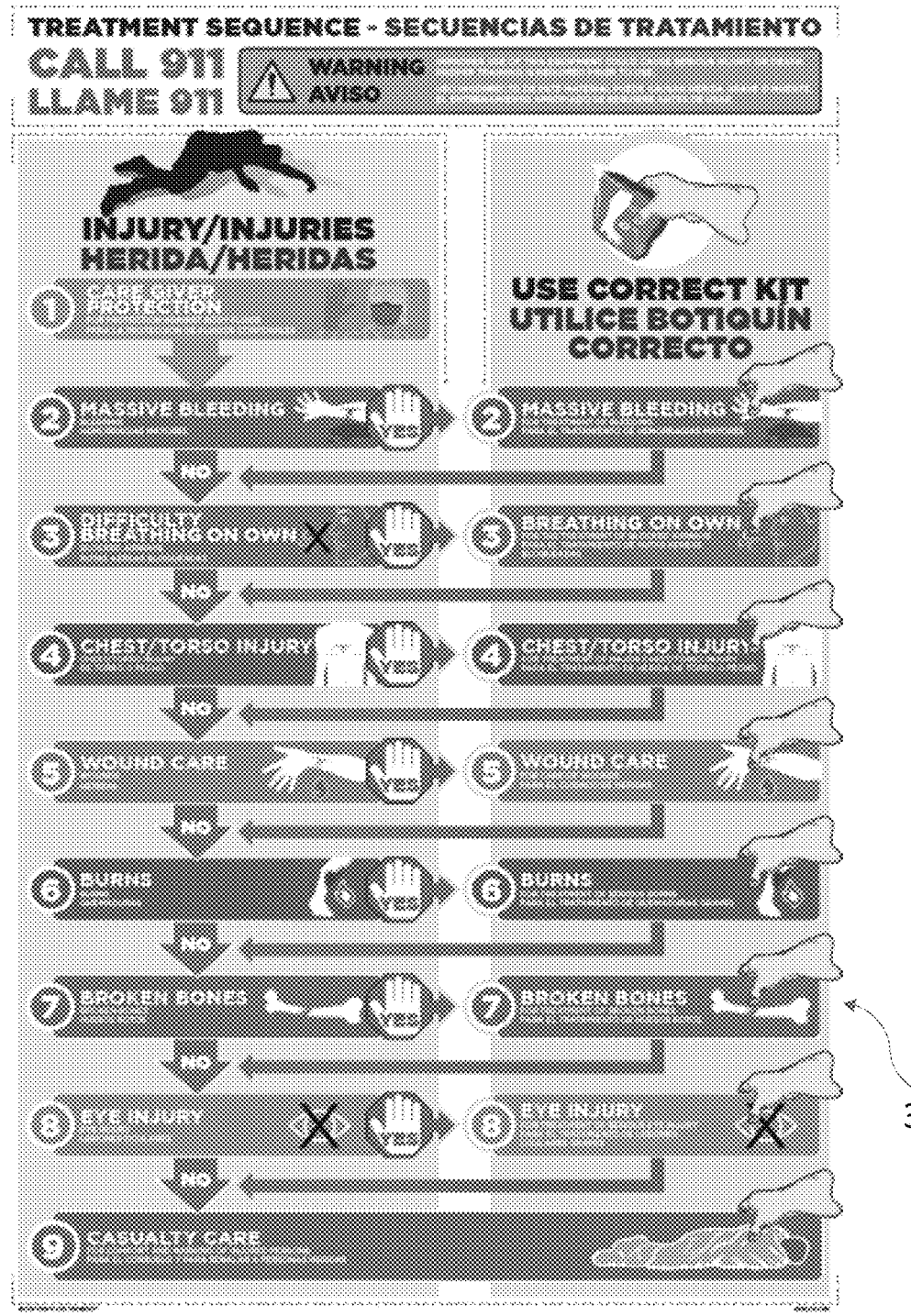
FIG. 2 illustrates the treatment sequence chart according to an embodiment of the invention.

FIG. 2 illustrates the treatment sequence chart 30 according to an embodiment of the invention. The treatment sequence chart 30 provides a flow chart that outlines the sequence of steps that a caregiver is to perform when providing treatment to a trauma victim. The treatment sequence chart 30 can be displayed on a large sheet of plastic, cardboard, or durable/laminated paper that can be physically attached to the case 20 via, for example, a clip, ring, or tether. The treatment sequence chart 30 can be placed on top of the medical packets 100-900, such that when a user opens the trauma kit 10, the treatment sequence chart 30 can be the first thing that the user sees, and can also be the first thing that the user picks up to review and follow. The surface area of the treatment sequence chart 30 can be slightly smaller than the surface area of the lid 26. Thus, the size and position of the treatment sequence chart 30 forces the user to see it. Moreover, the size and position of the treatment sequence chart 30 requires the user to physically touch it before the user can get to the medical packets.

In at least one embodiment of the invention, the treatment sequence chart 30 includes nine treatment steps: (1) Care Giver Protection; (2) Massive Bleeding; (3) Difficulty Breathing On Own; (4) Chest/Torso Injury; (5) Wound Care; (6) Burns; (7) Broken Bones; (8) Eye Injury; and (9) Casualty Care. It is recognized that in alternative embodiments, the treatment sequence chart can include more treatment steps, less treatment steps, combined treatment steps, or a different sequence of treatments steps.

Each treatment step in the treatment sequence chart 30 can include a pictorial representation of the treatment step. For example, a picture of a broken bone is displayed at treatment step (7). Each treatment step in the treatment sequence chart 30 can also include the name of the treatment step and/or a short textual description of the treatment step. For example, the text "Caregiver Protection" and "For Protection Against Bodily Fluids" is displayed at treatment step (1).

In at least one embodiment, as described more fully below, the pictorial representations of color-coded treatment steps, lack of detailed instructions for each treatment step, and flow sequence arrows can make the treatment sequence chart 30 simple and easy to follow at a macro level. Under stressful and time sensitive conditions, which are commonly associated with the treatment of trauma victims, an easy to follow instruction sheet can be the difference between life and death.

The treatment sequence chart 30 includes sequence numbers (1) to (9) that correspond to the treatment steps (1) to (9), where each treatment step refers to a single medical packet within the trauma kit 10. More specifically, each treatment step in the treatment sequence chart 30 is color and numerically coordinated to match to its corresponding medical packet within the trauma kit 10. For example, the treatment sequence chart 30 displays the massive bleeding treatment step in red labeled with the number "2" to match the red cover including the number "2" of the massive bleeding packet 200. This color and numeric coded scheme can make the treatment process of the trauma kit 10 easy to follow under stressful and time sensitive conditions.

As described more fully below, each of the medical packets 100-900 can include a color coded cover having a pictorial representation of the treatment step, the title of the treatment step, and/or a short description of the treatment step displayed thereon. For example, the caregiver protection packet 100 includes a forest green cover illustrating a caregiver wearing a glove, mask, and eye protection. This cover also includes the text "Caregiver Protection" and "For Protection Against Bodily Fluids".

As used herein, the term "cover" includes a flexible sheet inserted into a pouch of a medical packet. The cover could be a 3-panel sheet that is foldable in a book cover fashion to enclose the tools of the medical packet. Thus, the size, color, and position of the cover within the medical packet can make the medical packet highly visible and easily identifiable by a caregiver.

Each of the medical packets 100-900 includes instructions on the color coded cover. In another embodiment, the instructions are on a sheet that is separate from the cover. In order to assist a user in quickly identifying the appropriate tools within the medical kit, the instructions include treatments steps that are labeled with a number and a color. The tool that is to be used in the treatment step is color and number coded with the treatment step to allow for rapid identification of the tool by the user.

As described more fully below, the instructions can include a step-by-step pictorial representation of how to use the medical packet. In at least one embodiment, the instructions include written text to supplement the pictorial step-by-step instructions. In another embodiment, the instructions lack text, which can make the instructions easy to follow in situations where reading and comprehension of medical treatment instructions during stressful situations can be difficult. Omitting text from the instructions can also reduce clutter and simplify instructions when the text is in a language that is not comprehendible by the caregiver.

As illustrated towards the top of FIG. 2, the treatment sequence chart 30 begins with treatment step (1) Caregiver Protection. The treatment sequence chart 30 displays treatment step (1) Caregiver Protection in forest green with the number "1", which corresponds to the forest green cover (displaying the number "1") of caregiver protection packet 100. In at least one embodiment, the caregiver protection packet 100 includes a clear pouch for storing contents of the packet therein, the forest green cover/instruction card, gloves, masks, and eye shields.

Figure 3:
FIG. 3 illustrates a cover of a caregiver protection medical packet according to an embodiment of the invention.

FIG. 3 illustrates the cover 110 of the caregiver protection packet 100, which shows a caregiver wearing a glove, mask, and eye protection. The cover 110 also includes the name of the treatment step (i.e., "Caregiver Protection") and a short textual description of the treatment step in English and a second language (e.g., Spanish) (i.e., "For Protection Against Bodily Fluids", "Para La Proteccion De Liquidos De Cuerpo"). It is recognized in another embodiment that the cover of the caregiver protection packet can lack text.

Referring back to FIG. 1, from the treatment step (1) Caregiver Protection, the treatment sequence chart 30 continues to treatment step (2) Massive Bleeding. As illustrated in the treatment sequence chart 30, if the trauma victim has massive bleeding ("YES"), then the caregiver is instructed to go to the massive bleeding packet 200. The treatment sequence chart 30 displays treatment step (2) Massive Bleeding in red with the number "2", which corresponds to the red cover of massive bleeding packet 200 (displaying the number "2"). If the trauma victim does not have massive bleeding ("NO"), then the caregiver is instructed in the treatment sequence chart 30 to proceed to treatment step (3) Difficulty Breathing on Own.

Figure 4A:
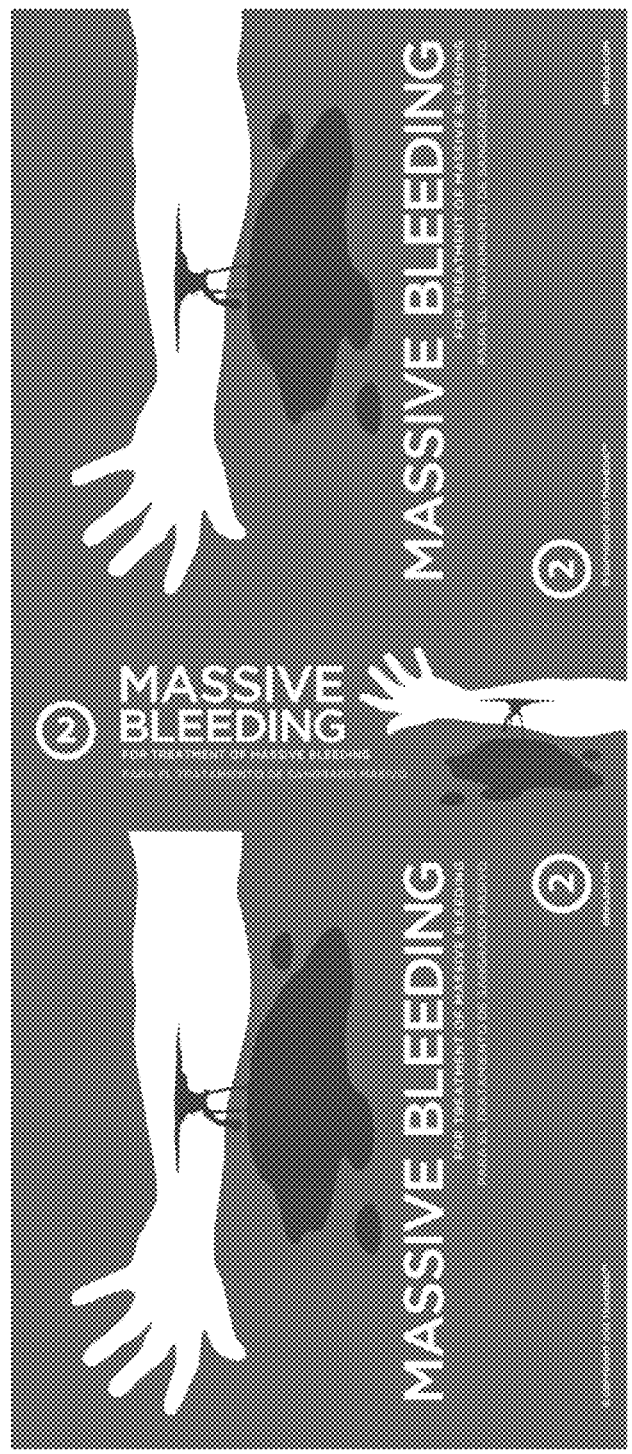
FIG. 4A is a front view illustrating a cover of a massive bleeding medical packet according to an embodiment of the invention.

The massive bleeding packet 200 can include a clear pouch for storing contents of the packet therein, a red cover/instruction card, at least one tourniquet, and at least one bandage package. FIG. 4A illustrates a front view of the cover 210 of the massive bleeding packet 200, which includes a pictorial representation of massive bleeding from a cut in a trauma victim's arm. The cover 210 also includes the name of the treatment step (i.e., "Massive Bleeding") and a short textual description of the treatment step in English and Spanish (i.e., "For Treatment of Massive Bleeding", "Para El Tratamiento De Sangrado Masivo"). It is recognized in another embodiment that the cover of the massive bleeding packet can lack text.

Figure 4B:
FIG. 4B is a rear view illustrating the cover shown in FIG. 4A according to an embodiment of the invention.

FIG. 4B illustrates a rear view of the cover 210, which includes step-by-step pictorial instructions for using the tourniquet and bandages. In another embodiment, the instructions are on a sheet of paper or card separate from the cover. Although the embodiment illustrated in FIG. 4B includes supplemental textual instructions, it is recognized in alternative embodiment that the instructions could lack text.

In at least one embodiment, the instructions include step 1 (labeled in orange with the number "1") and step 2 (labeled in green with the number "2"). This corresponds to the orange label with the number "1" on the tourniquet, and the green label with the number "2" on the bandage package. Thus, the color and numeric coding on the instructions and tools provide guidance to the user to assist the user in quickly locating the appropriate tools within the packet to treat the trauma victim.

Step 1 of the massive bleeding packet 200 includes the following sub-steps, which are shown as step-by-step pictorial instructions in FIG. 4B: unbuckle the tourniquet, wrap the tourniquet around a limb of the trauma victim, connect the buckle on the tourniquet, pull the tail of the tourniquet tight, twist the handle of the tourniquet, lock the handle in the triangle of the tourniquet, write the time that the tourniquet was placed on the trauma victim on the tourniquet, and place the trauma victim on his side.

In addition, step 2 of the massive bleeding packet 200 can include the following sub-steps, which are shown as step-by-step pictorial instructions in FIG. 4B: tear open bandage package, stretch out bandage, remove gauze from bandage package, place gauze on the trauma victim's wound, place the bandage on top of the gauze, wrap the bandage around the gauze, and place adhesive closure (e.g., medical tape) over the end of the bandage. It is recognized in alternative embodiments that the massive bleeding packet can include other tools/equipment for treating massive bleeding, and that the instructions can include more sub-steps, less sub-steps, a combination of sub-steps, and/or alternative sub-steps.

Referring back to FIG. 1, from the treatment step (2) Massive Bleeding, the treatment sequence chart 30 continues to treatment step (3) Difficulty Breathing on Own. As illustrated in the treatment sequence chart 30, if the trauma victim has difficulty breathing on his or her own ("YES"), then the caregiver is instructed to go to the difficulty breathing on own packet 300. The treatment sequence chart 30 displays treatment step (3) Difficulty Breathing on Own in blue with the number "3", which corresponds to the blue cover of difficulty breathing on own packet 300 (displaying the number "3"). If the trauma victim does not have difficulty breathing on his or her own ("NO"), then the caregiver is instructed in the treatment sequence chart 30 to proceed to the treatment step (4) Chest/Torso Injury.

Figure 5A:
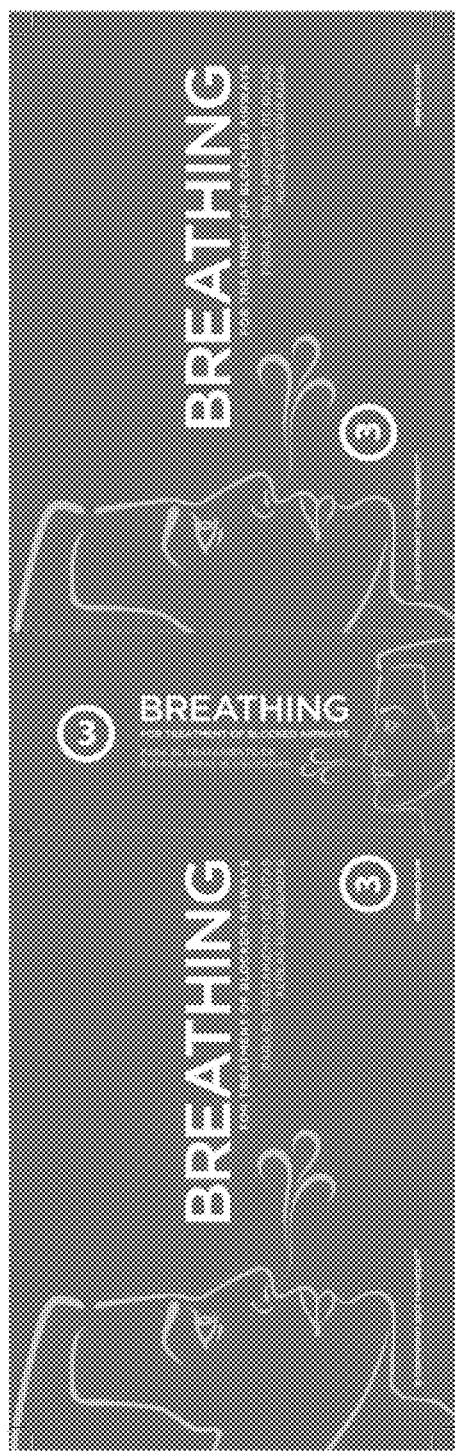
FIG. 5A is a front view illustrating a cover of a difficulty breathing on own medical packet according to an embodiment of the invention.

The difficulty breathing on own packet 300 can include a clear pouch for storing contents of the packet therein, a blue cover/instruction card, and a casualty blanket. FIG. 5A illustrates a front view of the cover 310 of the difficulty breathing on own packet 300, which includes a pictorial representation of a breath of air being emitted from the nose/mouth area of a person's face. The cover 310 also includes a shorthand name of the treatment step (i.e., "Breathing") and a short textual description of the treatment step in English and a second language (e.g., Spanish) (i.e., "For Treatment of Blocked Airways", "Para El Tratamiento De Retas Aereas Bloqueadas"). It is recognized in another embodiment that the cover of the difficulty breathing on own packet can lack text.

Figure 5B:
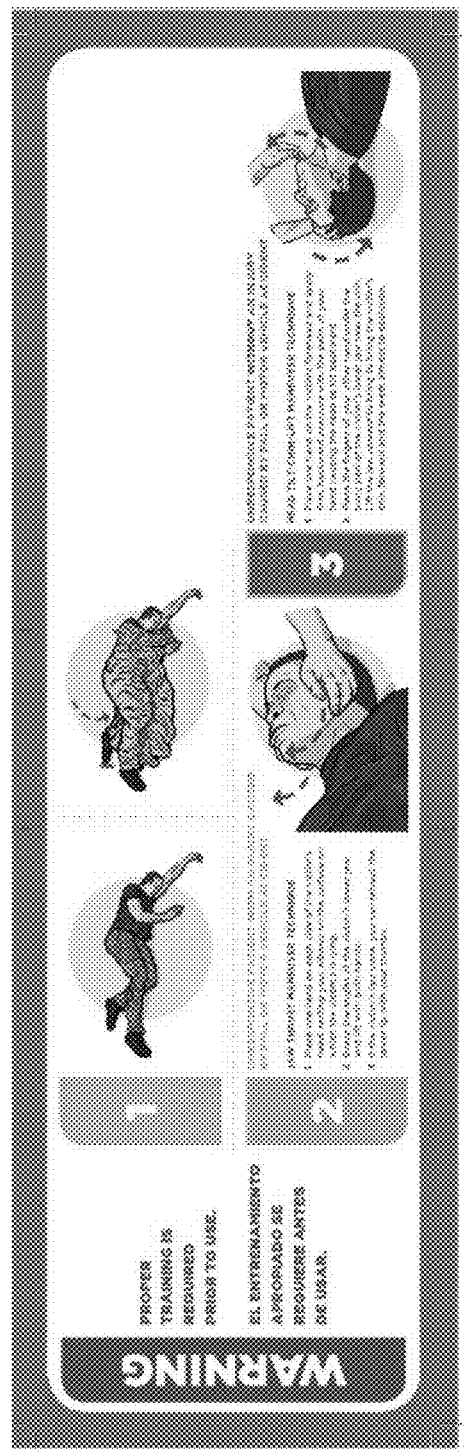
FIG. 5B is a rear view illustrating the cover shown in FIG. 5A according to an embodiment of the invention

FIG. 5B illustrates a rear view of the cover 310, which includes step-by-step pictorial instructions for using the difficulty breathing on own packet 300. In another embodiment, the instructions are on a sheet of paper or card separate from the cover. Although the embodiment illustrated in FIG. 5B includes textual instructions, it is recognized in alternative embodiment that the instructions could lack text.

In at least one embodiment, the instructions include step 1 (labeled in orange with the number "1") and step 2 (labeled in green with the number "2"). This corresponds to the orange label with the number "1" on the tourniquet, and the green label with the number "2" on the bandage package. Thus, the color and numeric coding on the instructions and tools provide guidance to the user assist the user in quickly locating the appropriate tools within the packet to treat the trauma victim.

In at least one embodiment, step 1 of the difficulty breathing on own packet 300 includes the following sub-steps, which are shown as step-by-step pictorial instructions in FIG. 5B: identify a trauma victim, and position the casualty blanket over the trauma victim by tucking portions of the body cover underneath the trauma victim.

Step 2 of the difficulty breathing on own packet 300 can include the following sub-steps, which are shown as step-by-step pictorial instructions in FIG. 5B: perform a jaw thrust maneuver technique if the trauma victim is unresponsive with an injury caused by fall or motor vehicle accident by placing one hand on each side of the trauma victim's head, resting your elbows on the surface on which the trauma victim is lying; grasping the angles of the trauma victim's lower jaw and lifting with both hands; and, if the trauma victim's lips are closed, retracting the lower lip with your thumbs.

Step 3 of the difficulty breathing on own packet 300 can include the following sub-steps, which are shown as step-by-step pictorial instructions in FIG. 5B: perform a head tilt-chin-lift maneuver technique if the trauma victim is unresponsive without an injury caused by fall or motor vehicle accident by placing one hand on the trauma victim's forehead and applying firm, backward pressure with the palm of your hand causing the trauma victim's head to tilt backward; and, placing the fingers of your other hand under the bony part of the trauma victim's lower jaw near the chin and lifting upward to bring the trauma victim's chin forward and the teeth almost to occlusion. It is recognized in alternative embodiments that the difficulty breathing on own packet can include other tools/equipment for treating the trauma patient, and that the instructions can include more sub-steps, less sub-steps, a combination of sub-steps, and/or alternative sub-steps.

Referring back to FIG. 1, from the treatment step (3) Difficulty Breathing on Own, the treatment sequence chart 30 continues to treatment step (4) Chest/Torso Injury. As illustrated in the treatment sequence chart 30, if the trauma victim has a chest/torso injury ("YES"), then the caregiver is instructed to go to the chest/torso injury packet 400. The treatment sequence chart 30 displays treatment step (4) Chest/Torso Injury in purple with the number "4", which corresponds to the purple cover of the chest/torso injury packet 400 (displaying the number "4"). If the trauma victim does not have a chest/torso injury ("NO"), then the caregiver is instructed in the treatment sequence chart 30 to proceed to the treatment step (5) Wound Care.

Figure 6A:
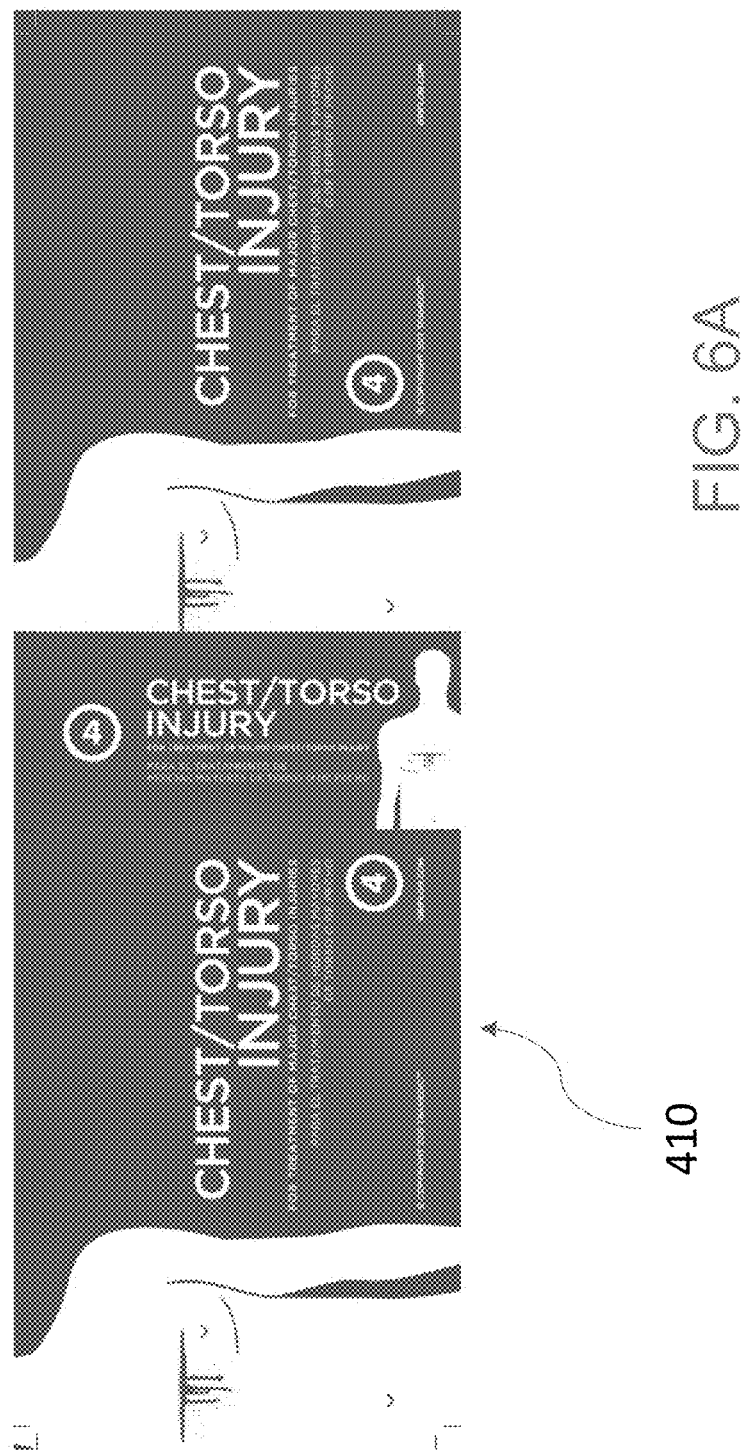
FIG. 6A is a front view illustrating a cover of a chest/torso injury medical packet according to an embodiment of the invention.

The chest/torso injury packet 400 can include a clear pouch for storing contents of the packet therein, a purple cover/instruction card, at least one gauze package, and medical tape. FIG. 6A illustrates a front view of the cover 410 of the chest/torso injury packet 400, which includes a pictorial representation of bleeding from a cut in a trauma victim's chest. The cover 410 also includes the name of the treatment step (i.e., "Chest/Torso Injury") and a short textual description of the treatment step in English and a second language (e.g., Spanish) (i.e., "For Treatment of Major Chest/Torso Injuries", "Para El Tratamiento De Heridas Mayores De Torso O De Pecho"). It is recognized in another embodiment that the cover of the chest/torso injury packet can lack text.

Figure 6B:
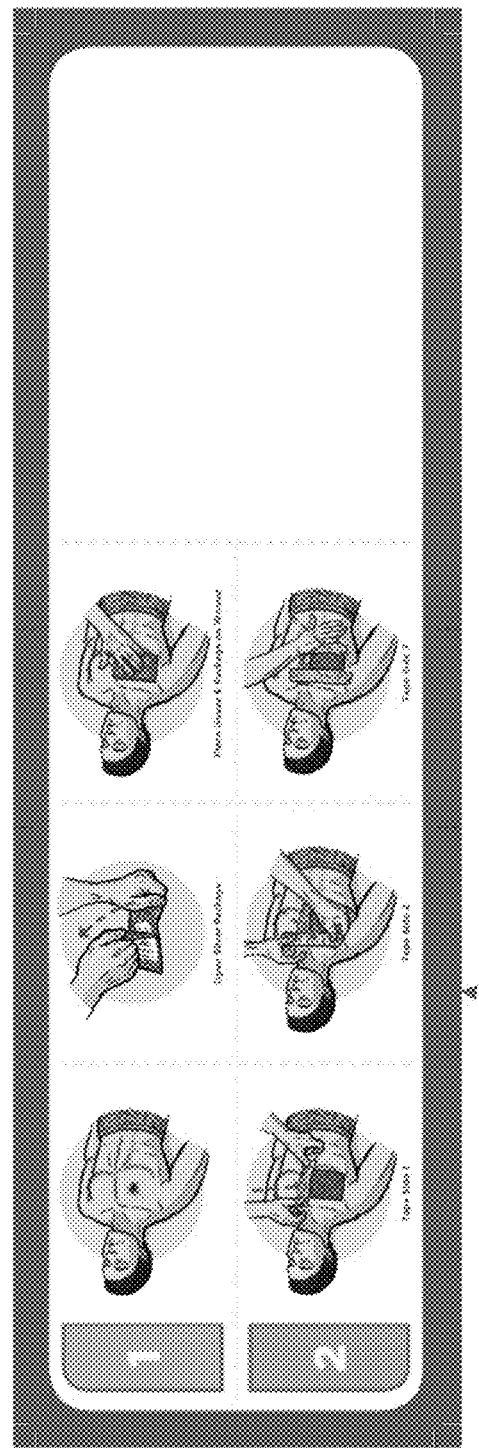
FIG. 6B is a rear view illustrating the cover shown in FIG. 6A according to an embodiment of the invention

FIG. 6B illustrates a rear view of the cover 410, which includes step-by-step pictorial instructions for using the gauze package and medical tape. In another embodiment, the instructions are on a sheet of paper or card separate from the cover. Although the embodiment illustrated in FIG. 6B includes supplemental textual instructions, it is recognized in alternative embodiment that the instructions could lack text.

In at least one embodiment, the instructions include step 1 (labeled in orange with the number "1") and step 2 (labeled in green with the number "2"). This corresponds to the orange label with the number "1" on the gauze packet, and the green label with the number "2" on the medical tape. Thus, the color and numeric coding on the instructions and tools provide guidance to the user assist the user in quickly locating the appropriate tools within the packet to treat the trauma victim.

In at least one embodiment, step 1 of the chest/torso injury packet 400 includes the following sub-steps, which are shown as step-by-step pictorial instructions in FIG. 6B: identify a wound to the chest/torso of a trauma victim, open the gauze package of the chest/torso injury packet 400, and place the gauze and gauze package on the wound.

Step 2 of the chest/torso injury packet 400 can include the following sub-steps, which are shown as step-by-step pictorial instructions in FIG. 6B: place medical tape on a first side of the gauze package, place medical tape on a second side of the gauze package, and place medical tape on a third side of the gauze package. It is recognized in alternative embodiments that the chest/torso injury packet can include other tools/equipment for treating chest/torso injuries, and that the instructions can include more sub-steps, less sub-steps, a combination of sub-steps, and/or alternative sub-steps.

Referring back to FIG. 1, from the treatment step (4) Chest/Torso Injury, the treatment sequence chart 30 continues to treatment step (5) Wound Care. As illustrated in the treatment sequence chart 30, if the trauma victim has needs wound care ("YES"), then the caregiver is instructed to go to the wound care packet 500. The treatment sequence chart 30 displays treatment step (5) Wound Care in brown with the number "5", which corresponds to the brown cover of the wound care packet 500 (displaying the number "5"). If the trauma victim does not need wound care ("NO"), then the caregiver is instructed in the treatment sequence chart 30 to proceed to the treatment step (6) Burns.

Figure 7A:
FIG. 7A is a front view illustrating a cover of a wound care medical packet according to an embodiment of the invention.

The wound care packet 500 can include a clear pouch for storing contents of the packet therein, a brown cover/instruction card, at least one first bandage package, and at least one second bandage package. FIG. 7A illustrates a front view of the cover 510 of the wound care packet 500, which includes a pictorial representation of bleeding and a drop of blood from a cut in a trauma victim's arm. The cover 510 also includes the name of the treatment step (i.e., "Wound Care") and a short textual description of the treatment step in English and a second language (e.g., Spanish) (i.e., "For Care of Wounds", "Para El Cuidado De Heridas"). It is recognized in another embodiment that the cover of the wound care packet can lack text.

Figure 7B:
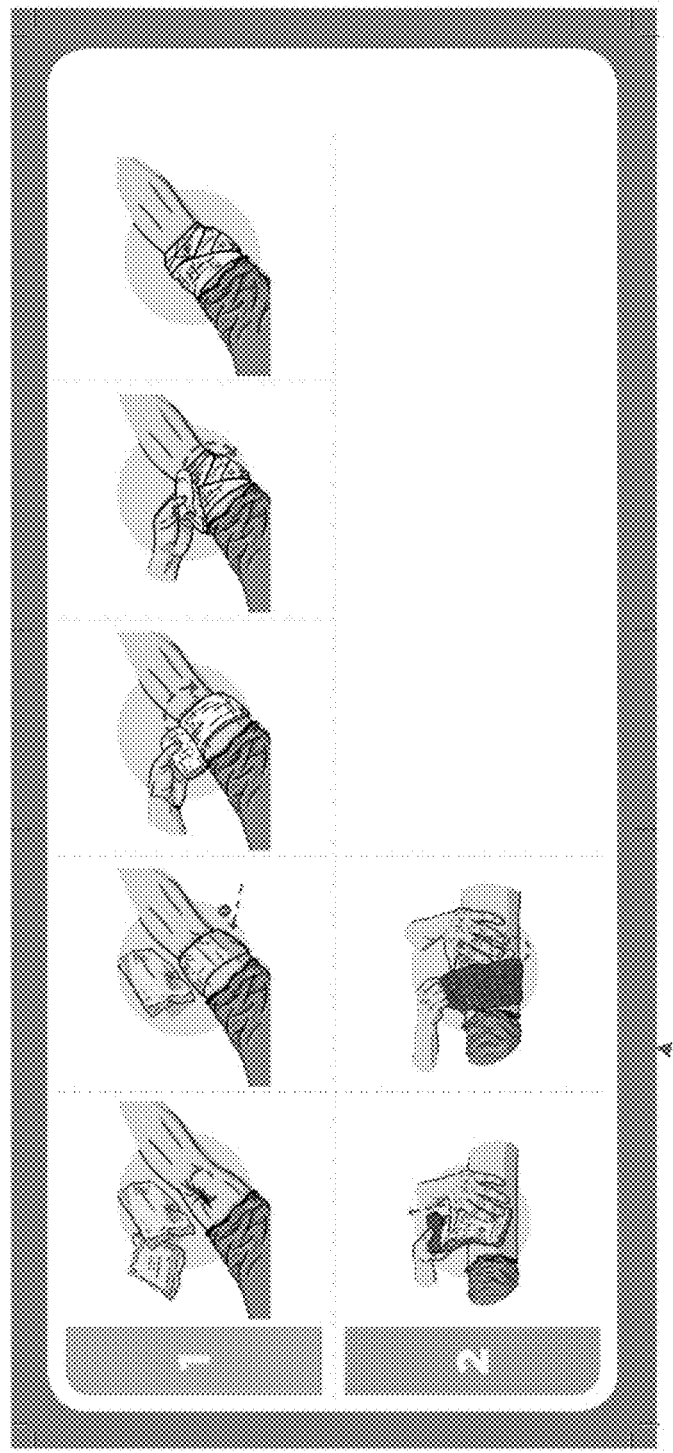
FIG. 7B is a rear view illustrating the cover shown in FIG. 7A according to an embodiment of the invention

FIG. 7B illustrates a rear view of the cover 510, which includes step-by-step pictorial instructions for using the first bandage package and second bandage package. In another embodiment, the instructions are on a sheet of paper or card separate from the cover. Although the embodiment illustrated in FIG. 7B lacks textual instructions, it is recognized in alternative embodiments that the instructions could include supplemental textual instructions.

In at least one embodiment, the instructions include step 1 (labeled in orange with the number "1") and step 2 (labeled in green with the number "2"). This corresponds to the orange label with the number "1" on the first bandage package, and the green label with the number "2" on the second bandage package. Thus, the color and numeric coding on the instructions and tools provide guidance to the user assist the user in quickly locating the appropriate tools within the packet to treat the trauma victim.

In at least one embodiment, step 1 of the wound care packet 500 includes the following sub-steps, which are shown as step-by-step pictorial instructions in FIG. 7B: separate the gauze and bandage from the first bandage package, place the gauze around the trauma victim's wound, wrap the bandage around the gauze and the trauma victim's wound, tuck one end of the bandage underneath a wrapped portion of the bandage (i.e., tuck the bandage underneath itself) to complete the wound care wrap.

In addition, step 2 of the wound care packet 500 can include the following sub-steps, which are shown as step-by-step pictorial instructions in FIG. 6B: place one end of the bandage in the second bandage package on the trauma victim's wound and stretch/unwrap the bandage, and wrap the bandage around itself and the trauma victim's wound. It is recognized in alternative embodiments that the wound care packet can include other tools/equipment for treating wounds, and that the instructions can include more sub-steps, less sub-steps, a combination of sub-steps, and/or alternative sub-steps.

Referring back to FIG. 1, from the treatment step (5) Wound Care, the treatment sequence chart 30 continues to treatment step (6) Burns. As illustrated in the treatment sequence chart 30, if the trauma victim has burns ("YES"), then the caregiver is instructed to go to the burns packet 600. The treatment sequence chart 30 displays treatment step (6) Burns in grey with the number "6", which corresponds to the grey cover of the burns packet 600 (displaying the number "6"). If the trauma victim does not have burns ("NO"), then the caregiver is instructed in the treatment sequence chart 30 to proceed to the treatment step (7) Broken Bones.

Figure 8A:
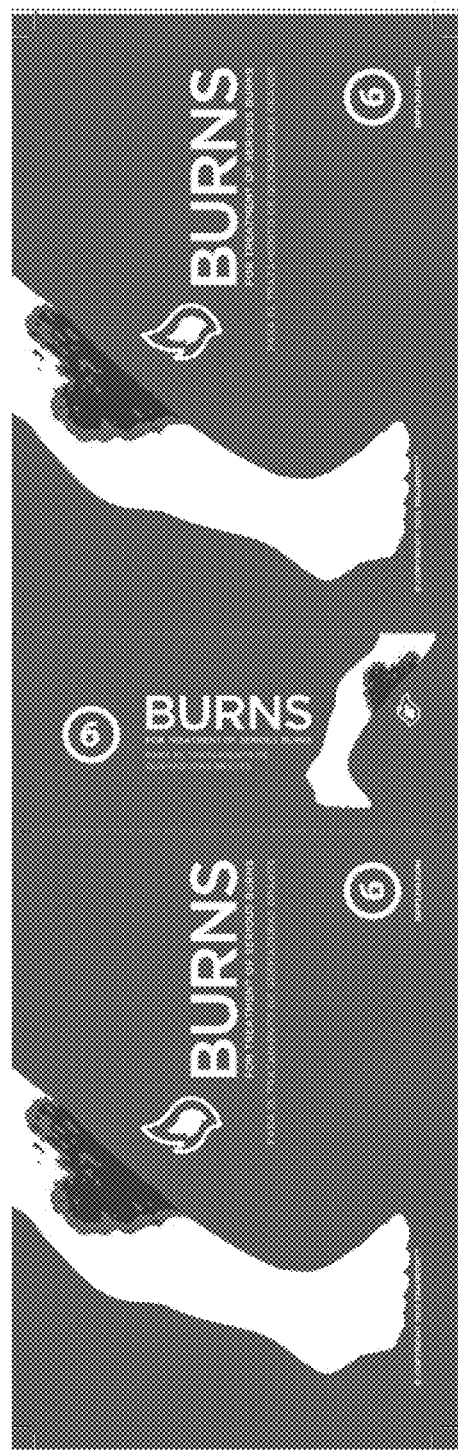
FIG. 8A is a front view illustrating a cover of a burns medical packet according to an embodiment of the invention.

The burns packet 600 can include a clear pouch for storing contents of the packet therein, a grey cover/instruction card, at least one first burns sub-packet, and at least one second burns sub-packet. FIG. 8A illustrates a front view of the cover 610 of the wound care packet 600, which includes a pictorial representation of a burn on the shin area of a trauma victim's leg. The cover 610 also includes the name of the treatment step (i.e., "Burns") and a short textual description of the treatment step in English and a second language (e.g., Spanish) (i.e., "For Treatment of Serious Burns", "Para El Tratamiento De Quemaduras Graves"). It is recognized in another embodiment that the cover of the burns packet can lack text.

Figure 8B:
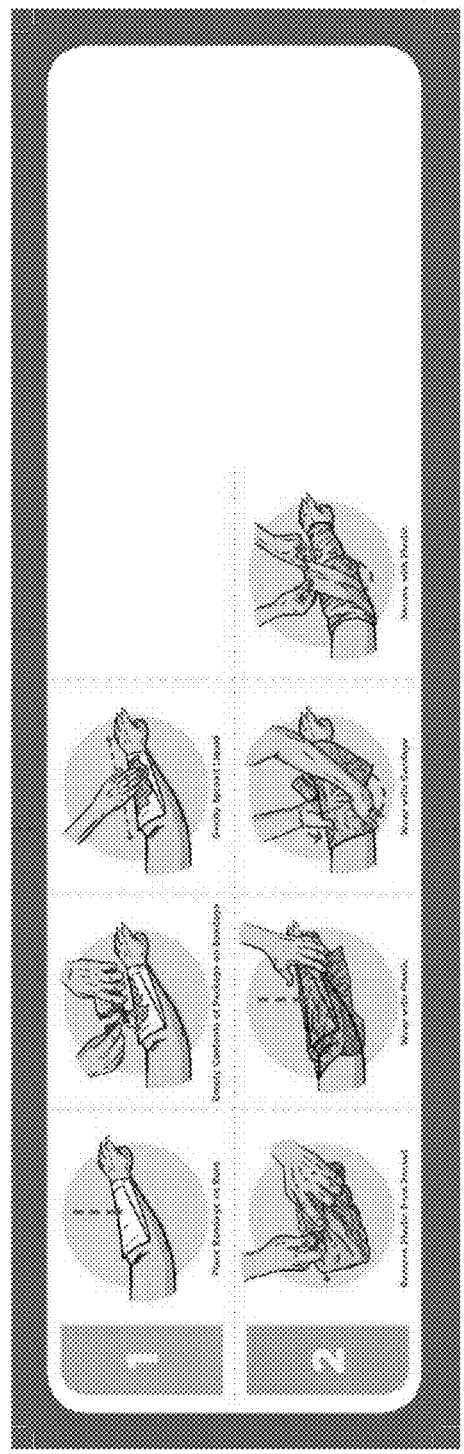
FIG. 8B is a rear view illustrating the cover shown in FIG. 8A according to an embodiment of the invention

FIG. 8B illustrates a rear view of the cover 610, which includes step-by-step pictorial instructions for using the first burns sub-packet and second burns sub-packet. In another embodiment, the instructions are on a sheet of paper or card separate from the cover. Although the embodiment illustrated in FIG. 8B includes textual instructions, it is recognized in alternative embodiments that the instructions could lack text.

In at least one embodiment, the instructions include step 1 (labeled in orange with the number "1") and step 2 (labeled in green with the number "2"). This corresponds to the orange label with the number "1" on the first burns sub-packet, and the green label with the number "2" on the second burns sub-packet. Thus, the color and numeric coding on the instructions and tools provide guidance to the user assist the user in quickly locating the appropriate tools within the packet to treat the trauma victim.

In at least one embodiment, step 1 of the burns packet 600 includes the following sub-steps, which are shown as step-by-step pictorial instructions in FIG. 8B: place a bandage from the first burns sub-packet on the trauma victim's burn, empty liquid contents of a burns treatment pouch from the first burns sub-packet onto the bandage, gently spread the liquid from the pouch onto the bandage.

In addition, step 2 of the burns packet 600 can include the following sub-steps, which are shown as step-by-step pictorial instructions in FIG. 8B: remove the plastic wrap from the pocket of the second burns sub-packet, wrap the plastic wrap around the trauma victim's burn, wrap the plastic wrap and the trauma victim's burn with a bandage from the second burns sub-packet, and secure the bandage and plastic wrap around the trauma victim's burn with elastic. It is recognized in alternative embodiments that the burns packet can include other tools/equipment for treating burns, and that the instructions can include more sub-steps, less sub-steps, a combination of sub-steps, and/or alternative sub-steps.

Referring back to FIG. 1, from the treatment step (6) Burns, the treatment sequence chart 30 continues to treatment step (7) Broken Bones. As illustrated in the treatment sequence chart 30, if the trauma victim has broken bones ("YES"), then the caregiver is instructed to go to the broken bones packet 700. The treatment sequence chart 30 displays treatment step (7) Broken Bones in olive green with the number "7", which corresponds to the olive green cover of the broken bones packet 700 (displaying the number "7"). If the trauma victim does not have broken bones ("NO"), then the caregiver is instructed in the treatment sequence chart 30 to proceed to the treatment step (8) Eye Injury.

Figure 9A:
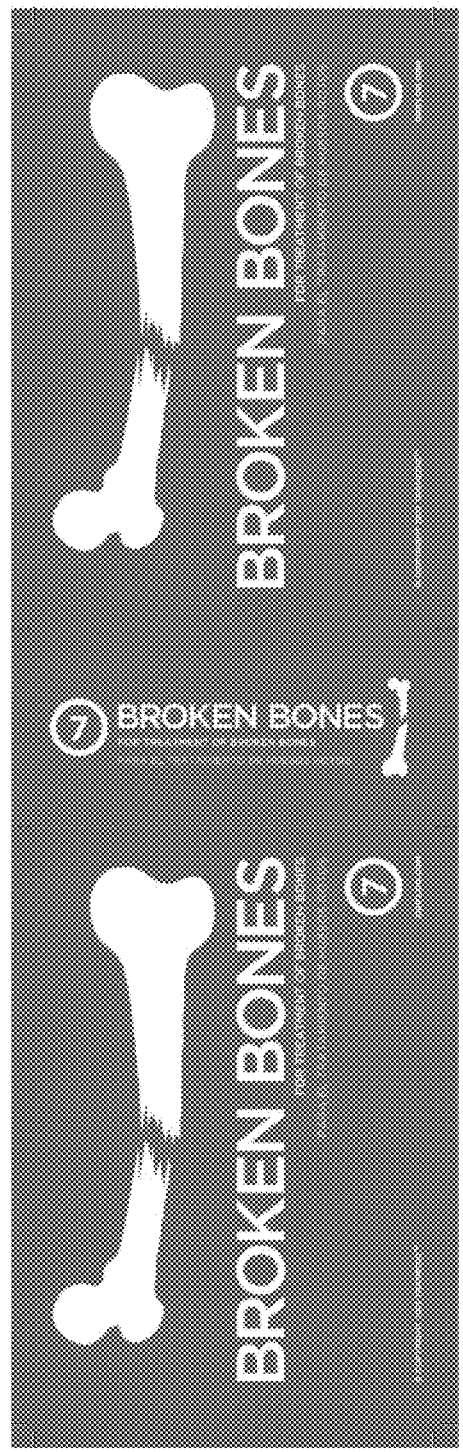
FIG. 9A is a front view illustrating a cover of a broken bones medical packet according to an embodiment of the invention.

The broken bones packet 700 can include a clear pouch for storing contents of the packet therein, an olive green cover/instruction card, at least one splint, and at least one bandage package. FIG. 9A illustrates a front view of the cover 710 of the broken bones packet 700, which includes a pictorial representation of a broken bone. The cover 710 also includes the name of the treatment step (i.e., "Broken Bones") and a short textual description of the treatment step in English and a second language (e.g., Spanish) (i.e., "For Treatment of Broken Bones", "Para El Tratamiento De Huesos Rotos"). It is recognized in another embodiment that the cover of the broken bones packet can lack text.

Figure 9B:
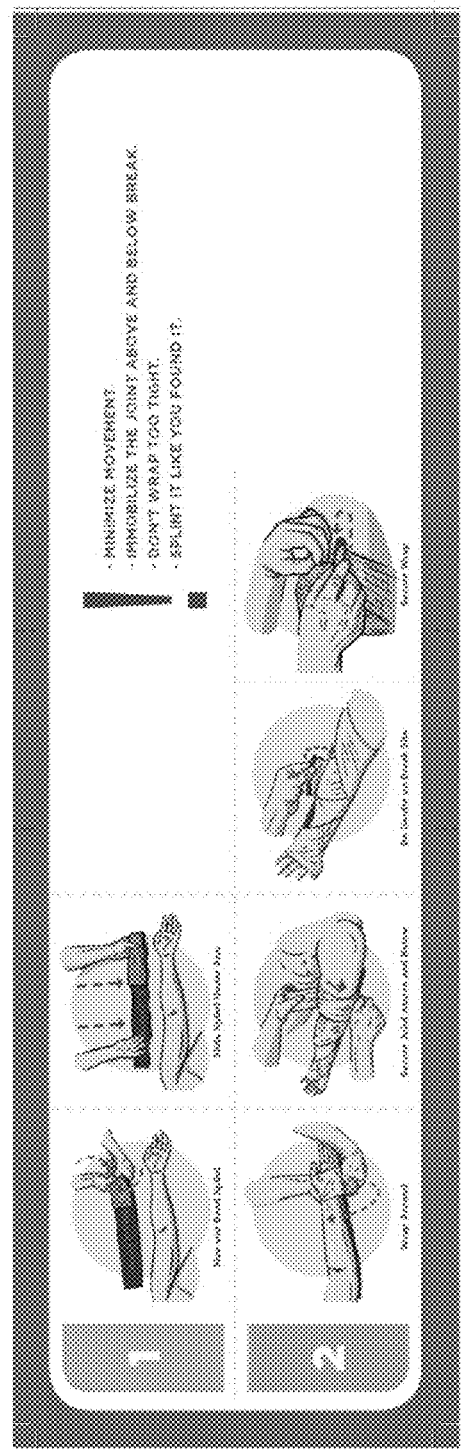
FIG. 9B is a rear view illustrating the cover shown in FIG. 9A according to an embodiment of the invention

FIG. 9B illustrates a rear view of the cover 710, which includes step-by-step pictorial instructions for using the splint and bandage package. In another embodiment, the instructions are on a sheet of paper or card separate from the cover. Although the embodiment illustrated in FIG. 9B includes textual instructions, it is recognized in alternative embodiments that the instructions could lack text.

In at least one embodiment, the instructions include step 1 (labeled in orange with the number "1") and step 2 (labeled in green with the number "2"). This corresponds to the orange label with the number "1" on the splint, and the green label with the number "2" on the bandage package. Thus, the color and numeric coding on the instructions and tools provide guidance to the user assist the user in quickly locating the appropriate tools within the packet to treat the trauma victim.

In at least one embodiment, step 1 of the broken bones packet 700 includes the following sub-steps, which are shown as step-by-step pictorial instructions in FIG. 9B: position the splint next to a wounded limb (e.g., arm) of the trauma victim to size and bend the splint, and slide the splint under the arm of the trauma victim.

Step 2 of the broken bones packet 700 can include the following sub-steps, which are shown as step-by-step pictorial instructions in FIG. 9B: wrap the bandage from the bandage packet around the splint, hand and wrist of the trauma victim, secure the joint above and below the break, be gentle on the break site as you wrap the bandage around the break site, and complete wrapping the bandage by securing the end of the bandage to the body of the bandage.

In one embodiment, the instructions on cover 710 include the following text:—MINIMIZE MOVEMENT.—IMMOBILIZE THE JOINT ABOVE AND BELOW BREAK.—DON'T WRAP TOO TIGHT.—SPLINT IT LIKE YOU FOUND IT. It is recognized in alternative embodiments that the broken bones packet can include other tools/equipment for treating broken bones, and that the instructions can include more sub-steps, less sub-steps, a combination of sub-steps, and/or alternative sub-steps.

Referring back to FIG. 1, from the treatment step (7) Broken Bones, the treatment sequence chart 30 continues to treatment step (8) Eye Injury. As illustrated in the treatment sequence chart 30, if the trauma victim has an eye injury ("YES"), then the caregiver is instructed to go to the eye injury packet 800. The treatment sequence chart 30 displays treatment step (8) Eye Injury in orange with the number "8", which corresponds to the orange cover of the eye injury packet 800 (displaying the number "8"). If the trauma victim does not have an eye injury ("NO"), then the caregiver is instructed in the treatment sequence chart 30 to proceed to the treatment step (9) Casualty Care.

Figure 10A:
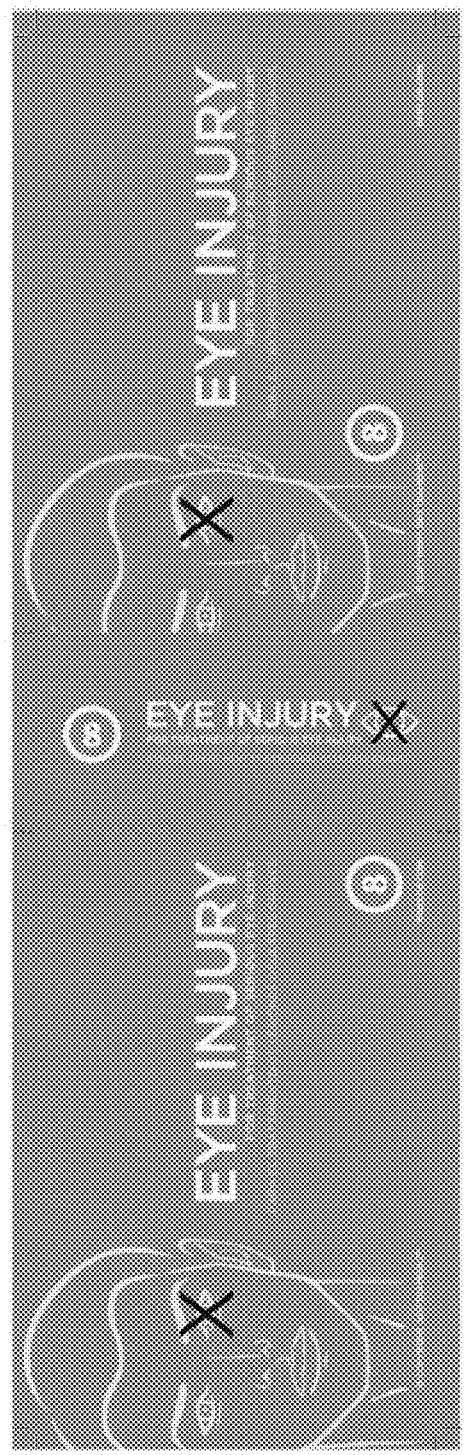
FIG. 10A is a front view illustrating a cover of an eye injury medical packet according to an embodiment of the invention.

The eye injury packet 800 can include a clear pouch for storing contents of the packet therein, an orange cover/instruction card, at least two eye shields, medical tape, at least one bandage, and at least one elastic cover. FIG. 10A illustrates a front view of the cover 810 of the eye injury packet 800, which includes a pictorial representation of a human face with an "X" over one of the eyes. The cover 810 also includes the name of the treatment step (i.e., "Eye Injury") and a short textual description of the treatment step in English and a second language (e.g., Spanish) (i.e., "For Treatment of Serious Eye Injury", "Para El Tratamiento De Lesiones Oculares Graves"). It is recognized in another embodiment that the cover of the eye injury packet can lack text.

Figure 10B:
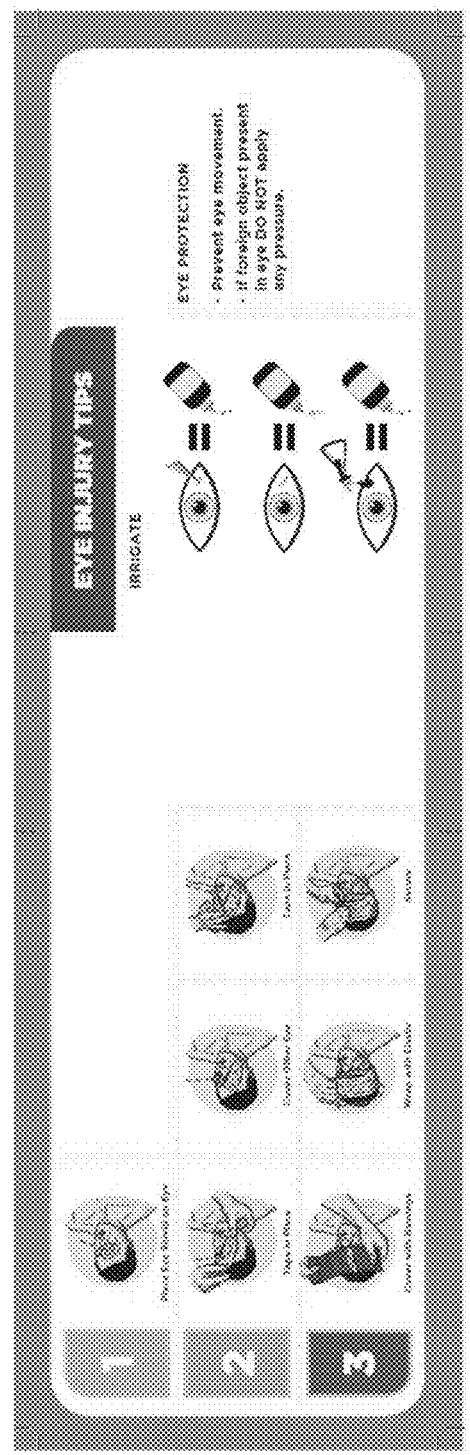
FIG. 10B is a rear view illustrating the cover shown in FIG. 10A according to an embodiment of the invention

FIG. 10B illustrates a rear view of the cover 810, which includes step-by-step pictorial instructions for using the eye shields, medical tape, bandage, elastic cover, and eye medical solution. In another embodiment, the instructions are on a sheet of paper or card separate from the cover. Although the embodiment illustrated in FIG. 10B includes textual instructions, it is recognized in alternative embodiments that the instructions could lack text.

In at least one embodiment, the instructions include step 1 (labeled in orange with the number "1"), step 2 (labeled in green with the number "2"), and step 3 (labeled in red with the number "3"). This corresponds to the orange label with the number "1" on the eye shields, the green label with the number "2" on the medical tape, and the red label with the number "3" on the bandage and elastic cover. Thus, the color and numeric coding on the instructions and tools provide guidance to the user assist the user in quickly locating the appropriate tools within the packet to treat the trauma victim.

In at least one embodiment, step 1 of the eye injury packet 800 includes the following pictorial instruction shown in FIG. 10B: place an eye shield on an eye of the trauma victim. Step 2 of the eye injury packet 800 can include the following sub-steps, which are shown as step-by-step pictorial instructions in FIG. 10B: tape the eye shield in place over the trauma victim's eye with medical tape, cover the other eye of the trauma victim with an additional eye shield, tape the additional eye shield in place over the trauma victim's other eye with medical tape.

Step 3 of the eye injury packet 800 can include the following sub-steps, which are shown as step-by-step pictorial instructions in FIG. 10B: cover the trauma victim's eyes with a bandage, wrap the trauma victim's eyes and the bandage with the elastic cover, and secure the eye shields, bandage, and elastic cover around the trauma victim's eyes by tucking the end of the elastic cover underneath the body of the elastic cover. It is recognized in alternative embodiments that the eye injury packet can include other tools/ equipment for treating eye injuries, and that the instructions can include more sub-steps, less sub-steps, a combination of sub-steps, and/or alternative sub-steps.

As illustrated in FIG. 10B, the cover 810 can include the following pictorial representations of eye injury tips: if a foreign object is in the trauma victim's eye=irrigate the trauma victim's eye with medical solution, if there is a cut in the trauma victim's eye=irrigate the trauma victim's eye with medical solution, and if the trauma victim's eye has come into contact with chemicals=irrigate the trauma victim's eye with medical solution. The cover 810 can also include the following textual eye injury tips:—Prevent eye movement.—if foreign object present in eye DO NOT apply any pressure.

Referring back to FIG. 1, from the treatment step (8) Eye Injury, the treatment sequence chart 30 continues to treatment step (9) Casualty Care. The treatment sequence chart 30 displays treatment step (9) Casualty Care in pink with the number "9", which corresponds to the pink cover of the casualty care packet 900 (displaying the number "9").

Figure 11A:
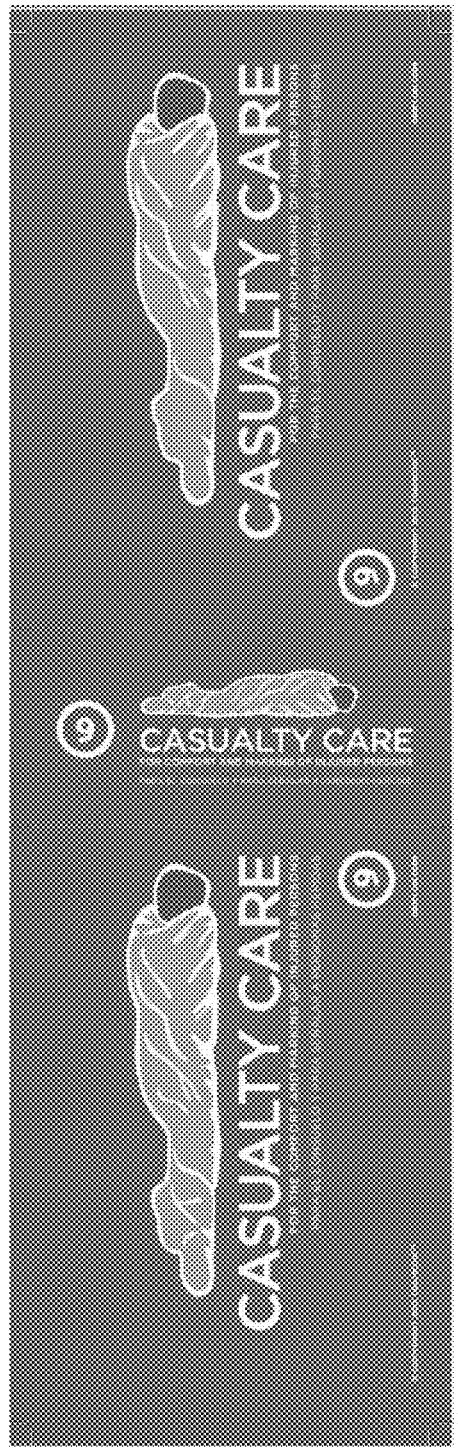
FIG. 11A is a front view illustrating a cover of a casualty care medical packet according to an embodiment of the invention.

The casualty care packet 900 can include a clear pouch for storing contents of the packet therein, a pink cover/instruction card, and at least one casualty blanket. FIG. 11A illustrates a front view of the cover 910 of the casualty care packet 900, which includes a pictorial representation of a trauma victim in a casualty blanket. The cover 910 also includes the name of the treatment step (i.e., "Casualty Care") and a short textual description of the treatment step in English and a second language (e.g., Spanish) (i.e., "For the Comfort and Marking of Injured Persons", "Para El Consuelo Y Para Senalar a Personas Heridas"). It is recognized in another embodiment that the cover of the casualty care packet can lack text.

Figure 11B:
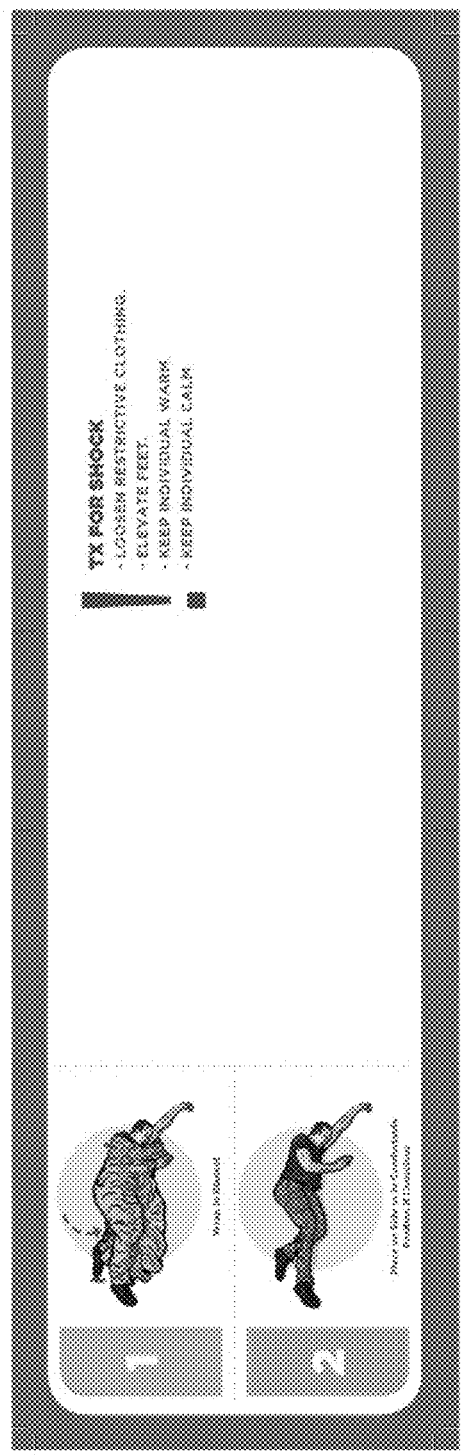
FIG. 11B is a rear view illustrating the cover shown in FIG. 11A according to an embodiment of the invention.

FIG. 11B illustrates a rear view of the cover 910, which includes step-by-step pictorial instructions for using the casualty care packet 900. In another embodiment, the instructions are on a sheet of paper or card separate from the cover. Although the embodiment illustrated in FIG. 11B includes textual instructions, it is recognized in alternative embodiments that the instructions could lack text.

In at least one embodiment, step 1 of the casualty care packet 900 includes the following pictorial instruction shown in FIG. 11B: wrap the trauma victim in the casualty blanket by tucking portions of the casualty blanket underneath the trauma victim. Step 2 of the casualty care packet 900 can include the following pictorial instruction shown in FIG. 11B: place the trauma victim on his (or her) side or in a comfortable position if the trauma victim is conscious.

It is recognized in alternative embodiments that the casualty care packet can include other tools/equipment for casualty care, and that the instructions can include more sub-steps, less sub-steps, a combination of sub-steps, and/or alternative sub-steps. The cover 910 can also include the following textual casualty care tips:—LOOSEN RESTRICTIVE CLOTHING.—ELEVATE FEET.—KEEP INDIVIDUAL WARM.—KEEP INDIVIDUAL CALM.

At least one embodiment of the invention provides a trauma kit including a plurality of medical packets, wherein the medical packets include a caregiver protection packet, a massive bleeding packet, a breathing packet, a torso injury packet, a wound packet, a burns packet, a broken bones packet, an eye injury packet, and a casualty care packet. One or more of the medical packets can include treatment instructions, a first tool for treating a particular medical situation, the first tool being labeled in a first color, and a second tool for treating the particular medical situation, the second tool being labeled in a second color different from the first color. In at least one embodiment, the first tool is labeled with the first character, and the second tool is labeled with the second character.

The treatment instructions can include a sequence of pictorial diagrams providing step-by-step instructions for using the one or more of the medical packets. More specifically, the treatment instructions can include a first treatment instruction labeled with a first character designated in the first color, such that the first treatment instruction is color-coded to the first tool for rapid identification by a user. The treatment instructions can further include a second treatment instruction labeled with a second character designated in the second color, such that the second treatment instruction is color-coded to the second tool for rapid identification by the user.

In at least one embodiment, a medical packet includes one or more additional tools for treating the particular medical situation, wherein each of the additional tool(s) are labeled in an additional color different from the first color and the second color. The treatment instructions can include one or more additional treatment instructions labeled with an additional character designated in the additional color, such that the additional treatment instruction is color-coded to the additional tool for rapid identification by the user.

The trauma kit can also include a treatment sequence chart including a flow diagram of treatment steps, wherein each of the treatment steps are color-coded to one of the medical packets. Each of the treatment steps on the treatment sequence chart can include a pictorial representation of the treatment step; and, each of the medical packets can include a pictorial representation of the treatment step that the medical packet corresponds to.

Additionally, the trauma kit can include a case including one or more divider for forming multiple storage compartments within an interior of the case. The divider(s) can be moveable to adjust the sizes of the storage compartments. The treatment sequence chart can be physically attached to the case, wherein a surface area of the treatment sequence chart in a folded configuration is larger than an open area of at least one of the compartments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A trauma kit comprising:
a plurality of medical packets,
wherein at least one of said medical packets includes:
a first tool for treating a medical situation, said first tool being labeled in a first color,
a second tool for treating the medical situation, said second tool being labeled in a second color, and
treatment instructions including:
a first treatment instruction labeled with a first character designated in the first color, and
a second treatment instruction labeled with a second character designated in the second color; and
a treatment sequence chart including a flow diagram of treatment steps, wherein each of the treatment steps are color-coded to one of said medical packets.

2. The trauma kit according to claim 1, wherein said first tool is labeled with the first character, and wherein said second tool is labeled with the second character.

3. The trauma kit according to claim 1, wherein the at least one of said medical packets includes at least one additional tool for treating the medical situation, said additional tool being labeled in an additional color, and wherein said treatment instructions include at least one additional treatment instruction labeled with an additional character designated in the additional color.

4. The trauma kit according to claim 1, wherein said treatment instructions include a sequence of pictorial diagrams providing step-by-step instructions for using the at least one of said medical packets.

5. The trauma kit according to claim 1, wherein each of the treatment steps on said treatment sequence chart includes a pictorial representation of the treatment step, and wherein each of said medical packets include a pictorial representation of the treatment step that the medical packet corresponds to.

6. The trauma kit according to claim 1, further comprising a case including at least one divider for forming multiple storage compartments within an interior of said case.

7. The trauma kit according to claim 6, wherein said divider is moveable to adjust the sizes of said storage compartments.

8. The trauma kit according to claim 6, wherein said treatment sequence chart is physically attached to said case.

9. The trauma kit according to claim 6, wherein a surface area of said treatment sequence chart is larger than an open area of at least one of said compartments.

10. The trauma kit according to claim 1, wherein said medical packets include a caregiver protection packet, a massive bleeding packet, a breathing packet, a torso injury packet, a wound packet, a burns packet, a broken bones packet, an eye injury packet, and a casualty care packet.

11. A trauma kit comprising:
a plurality of medical packets,
wherein at least one of said medical packets includes:
a first tool for treating a particular medical situation, said first tool being labeled with a first character and in a first color,
a second tool for treating the particular medical situation, said second tool being labeled with a second character and in a second color different from the first color, and
treatment instructions including a sequence of pictorial diagrams providing step-by-step instructions for using the at least one of said medical packets, said treatment instructions including:
a first treatment instruction labeled with the first character designated in the first color, such that the first treatment instruction is color-coded to said first tool for rapid identification by a user, and
a second treatment instruction labeled with the second character designated in the second color, such that the second treatment instruction is color-coded to said second tool for rapid identification by the user; and
a treatment sequence chart including a flow diagram of treatment steps, wherein each of the treatment steps are color-coded to one of said medical packets.

12. The trauma kit according to claim 11, wherein the at least one of said medical packets includes at least one additional tool for treating the particular medical situation, said additional tool being labeled in an additional color different from the first color and the second color, and wherein said treatment instructions include at least one additional treatment instruction labeled with an additional character designated in the additional color, such that the additional treatment instruction is color-coded to said additional tool for rapid identification by the user.

13. The trauma kit according to claim 11, wherein each of the treatment steps on said treatment sequence chart includes a pictorial representation of the treatment step, and wherein each of said medical packets include a pictorial representation of the treatment step that the medical packet corresponds to.

14. The trauma kit according to claim 11, further comprising a case including at least one divider for forming multiple storage compartments within an interior of said case.

15. The trauma kit according to claim 14, wherein said divider is moveable to adjust the sizes of said storage compartments.

16. The trauma kit according to claim 14, wherein said treatment sequence chart is physically attached to said case.

17. The trauma kit according to claim 14, wherein a surface area of said treatment sequence chart in a folded configuration is larger than an open area of at least one of said compartments.

18. The trauma kit according to claim 11, wherein said medical packets include a caregiver protection packet, a massive bleeding packet, a breathing packet, a torso injury packet, a wound packet, a burns packet, a broken bones packet, an eye injury packet, and a casualty care packet.

19. A kit comprising:
a treatment sequence chart including a flow diagram of treatment steps, wherein the treatment steps include caregiver protection displayed in a first color, treatment for massive bleeding displayed in a second color, treatment for breathing displayed in a third color, treatment for torso injury displayed in a fourth color, treatment for wounds displayed in a fifth color, treatment for burns displayed in a sixth color, treatment for broken bones displayed in a seventh color, treatment for eye injuries displayed in an eighth color, and casualty care displayed in a ninth color;
a caregiver protection packet including: a first cover in the first color, at least one tool for providing caregiver protection and having a first label in a first label color, first treatment instructions having at least one instruction labeled with a character designated in the color of the first label, and including at least one pictorial diagram providing instructions for using said caregiver protection packet;

a massive bleeding packet including: a second cover in the second color, at least one tool for treating massive bleeding and having a second label in a second label color, and second treatment instructions having at least one instruction labeled with a character designated in the color of the second label, and including a sequence of pictorial diagrams providing step-by-step instructions for using said massive bleeding packet;

a breathing packet including: a third cover in the third color, at least one tool for treating a patient having difficulty breathing and having a third label in a third label color, and third treatment instructions having at least one instruction labeled with a character designated in the color of the third label, and including a sequence of pictorial diagrams providing step-by-step instructions for using said breathing packet;

a torso injury packet including: a fourth cover in the fourth color, at least one tool for treating a patient having a torso injury and having a fourth label in a fourth label color, and fourth treatment instructions having at least one instruction labeled with a character designated in the color of the fourth label, and including a sequence of pictorial diagrams providing step-by-step instructions for using said torso injury packet;

a wound packet including: a fifth cover in the fifth color, at least one tool for treating a patient having a wound and having a fifth label in a fifth label color, and fifth treatment instructions having at least one instruction labeled with a character designated in the color of the fifth label, and including a sequence of pictorial diagrams providing step-by-step instructions for using said wound packet;

a burns packet including: a sixth cover in the sixth color, at least one tool for treating a patient having a burn and having a sixth label in a sixth label color, and sixth treatment instructions having at least one instruction labeled with a character designated in the color of the sixth label, and including a sequence of pictorial diagrams providing step-by-step instructions for using said burns packet;

a broken bones packet including: a seventh cover in the seventh color, at least one tool for treating a patient having a broken bone and having a seventh label in a seventh label color, and seventh treatment instructions having at least one instruction labeled with a character designated in the color of the seventh label, and including a sequence of pictorial diagrams providing step-by-step instructions for using said broken bones packet;

an eye injury packet including: an eighth cover in the eighth color, at least one tool for treating a patient having an eye injury and having an eighth label in an eighth label color, and eighth treatment instructions having at least one instruction labeled with a character designated in the color of the eighth label, and including a sequence of pictorial diagrams providing step-by-step instructions for using said eye injury packet; and a casualty care packet including: a ninth cover in the ninth color, at least one tool for caring for a casualty victim and having a ninth label in a ninth label color, and ninth treatment instructions having at least one instruction labeled with a character designated in the color of the ninth label, and including a sequence of pictorial diagrams providing step-by-step instructions for using said casualty care packet.

20. The kit according to claim 19, wherein each treatment step on said treatment sequence chart includes a pictorial representation of the treatment step, and wherein each cover that corresponds to each treatment step on said treatment sequence chart includes the respective pictorial representation of the treatment step.

21. The kit according to claim 2, wherein the first and second characters are numbers.

22. The kit according to claim 11, wherein the treatment sequence chart further includes a plurality of numbers each corresponding to a respective treatment step of the flow diagram.

23. The kit according to claim 22, wherein each number has a color corresponding to the color-coding.

24. The kit according to claim 11, wherein at least one of the medical packets includes treatment instructions folded around tools included in the at least one medical packet.

* * * * *